(12) United States Patent
Matsumoto et al.

(10) Patent No.: US 10,302,612 B2
(45) Date of Patent: May 28, 2019

(54) HYDROGEN CONCENTRATION MEASURING DEVICE

(71) Applicants: STANLEY ELECTRIC CO., LTD., Meguro-ku, Tokyo (JP); TOKYO UNIVERSITY OF SCIENCE FOUNDATION, Shinjuku-ku, Tokyo (JP)

(72) Inventors: Koji Matsumoto, Tokyo (JP); Masakazu Satsu, Tokyo (JP); Takanori Aimono, Tokyo (JP); Keiichi Ikegami, Tokyo (JP); Shinichi Uozumi, Tokyo (JP); Keishi Nishio, Tokyo (JP); Yuki Yamaguchi, Tokyo (JP)

(73) Assignees: STANLEY ELECTRIC CO., LTD., Tokyo (JP); TOKYO UNIVERSITY OF SCIENCE FOUNDATION, Tokyo (JP)

( * ) Notice: Subject to any disclaimer, the term of this patent is extended or adjusted under 35 U.S.C. 154(b) by 304 days.

(21) Appl. No.: 15/382,446

(22) Filed: Dec. 16, 2016

(65) Prior Publication Data

US 2017/0176403 A1   Jun. 22, 2017

(30) Foreign Application Priority Data

Dec. 21, 2015   (JP) ................................ 2015-249018

(51) Int. Cl.
*G01N 33/00* (2006.01)
*G01N 27/04* (2006.01)
(52) U.S. Cl.
CPC .......... *G01N 33/005* (2013.01); *G01N 27/04* (2013.01); *G01N 33/0032* (2013.01)
(58) Field of Classification Search
CPC ............. G01N 33/0027; G01N 33/005; G01N 33/0031; G01N 33/0032
See application file for complete search history.

(56) References Cited

U.S. PATENT DOCUMENTS 4,836,012 A * 6/1989 Doty .................. G01N 33/0027
                                                      136/255
5,279,795 A    1/1994 Hughes et al.
(Continued)

FOREIGN PATENT DOCUMENTS

DE    102004060103 A1   12/2005
EP        2594937 A1    5/2013
JP       2007057233 A   3/2007

OTHER PUBLICATIONS

Prinz, Jan, et al. "Combined light and electron scattering for exploring hydrogen in thin metallic films." Applied Physics Letters 97.25 (2010):251910.*

(Continued)

*Primary Examiner* — Son T Le
*Assistant Examiner* — Alexander A Mercado
(74) *Attorney, Agent, or Firm* — Holtz, Holtz & Volek PC

(57) ABSTRACT

Provided is a hydrogen concentration measuring device capable of measuring with high accuracy a hydrogen concentration over an extensive range by a simple configuration. The device includes: a sensor chip which detects the electric resistance of a sensing film; an optical measurement unit which detects the transmitted light intensity of the film; and a controller. The controller performs measurement processing such that a hydrogen concentration in the gas atmosphere is measured based on the detected electric resistance in a first measurement range and based on the detected transmitted light intensity in a second measurement range and is determined so as to reduce a difference between the hydrogen concentration based on the detected electric resistance and the hydrogen concentration based on the detected transmitted light intensity in the overlap of the first measurement range and the second measurement range.

5 Claims, 8 Drawing Sheets

(56) References Cited

U.S. PATENT DOCUMENTS

| | | | | |
|---|---|---|---|---|
| 2005/0072673 A1* | 4/2005 | Fukuda | ............... | G01N 33/005 |
| | | | | 204/424 |
| 2005/0186117 A1* | 8/2005 | Uchiyama | ............ | G01N 21/783 |
| | | | | 422/91 |
| 2005/0284208 A1 | 12/2005 | Oishi et al. | | |
| 2007/0209937 A1* | 9/2007 | Hoagland | ............ | G01N 27/122 |
| | | | | 204/424 |
| 2009/0302857 A1* | 12/2009 | Harada | ............. | G01N 27/4074 |
| | | | | 324/444 |
| 2010/0050744 A1* | 3/2010 | Petrovic | ............ | G01N 21/3504 |
| | | | | 73/31.06 |
| 2010/0077840 A1* | 4/2010 | Srivastava | ........... | G01N 27/305 |
| | | | | 73/31.05 |
| 2010/0290050 A1* | 11/2010 | Uchiyama | .............. | B82Y 30/00 |
| | | | | 356/445 |
| 2013/0219990 A1* | 8/2013 | Allmendinger | .... | G01N 33/0027 |
| | | | | 73/23.31 |
| 2013/0258347 A1* | 10/2013 | Satterfield | .............. | G01N 21/55 |
| | | | | 356/445 |
| 2016/0061761 A1* | 3/2016 | Shim | ................... | G01N 27/122 |
| | | | | 506/7 |
| 2017/0261485 A1* | 9/2017 | Panella | ............... | G01N 33/005 |
| 2017/0276627 A1* | 9/2017 | Dobrokhotov | ....... | G01N 27/125 |
| 2018/0045699 A1* | 2/2018 | Thar | ...................... | G01N 21/63 |
| 2018/0059021 A1* | 3/2018 | Yeh | ........................ | G01N 21/61 |

OTHER PUBLICATIONS

Extended European Search Report (EESR) dated Apr. 19, 2017 issued in counterpart European Application No. 16204765.8.

* cited by examiner

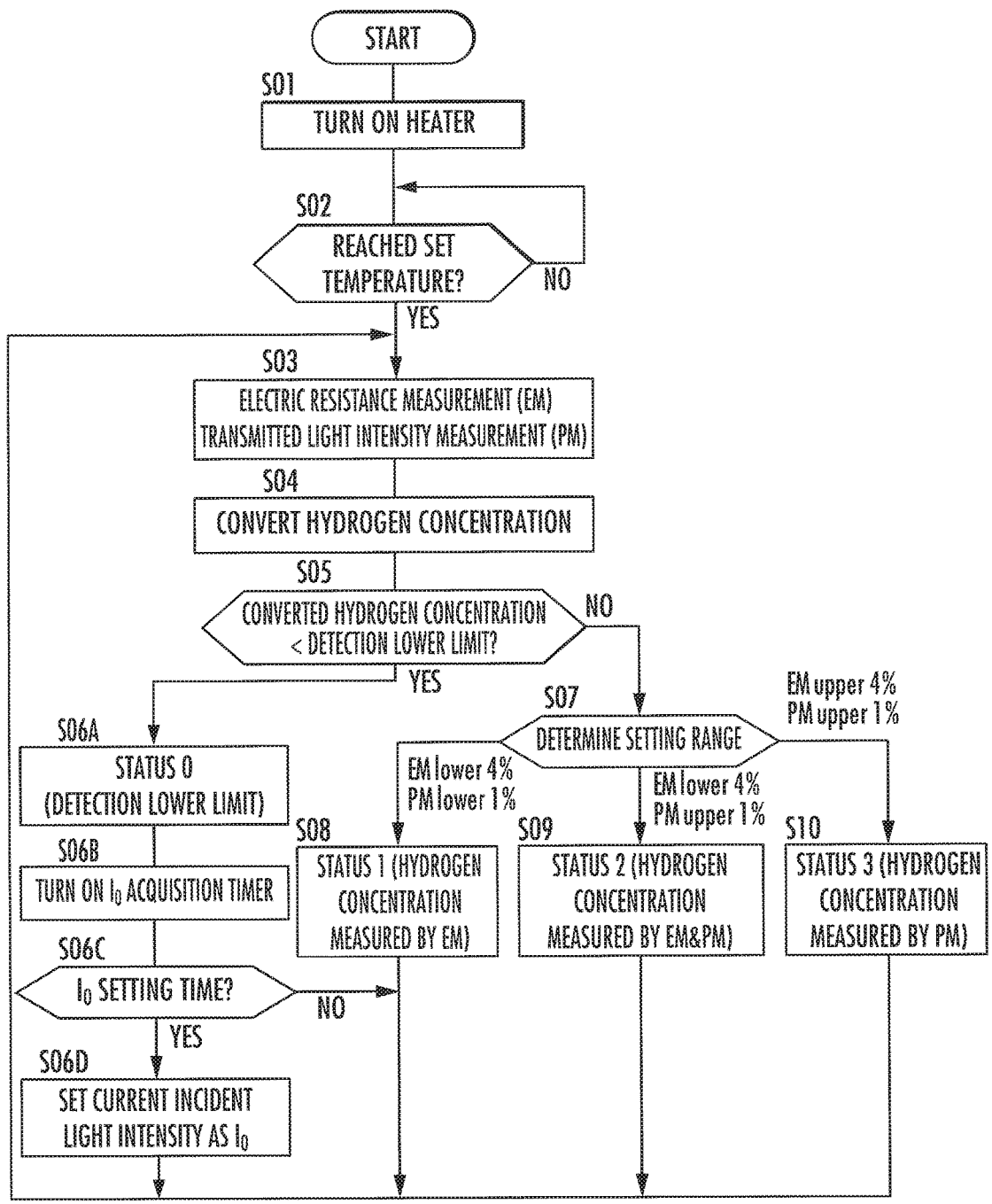

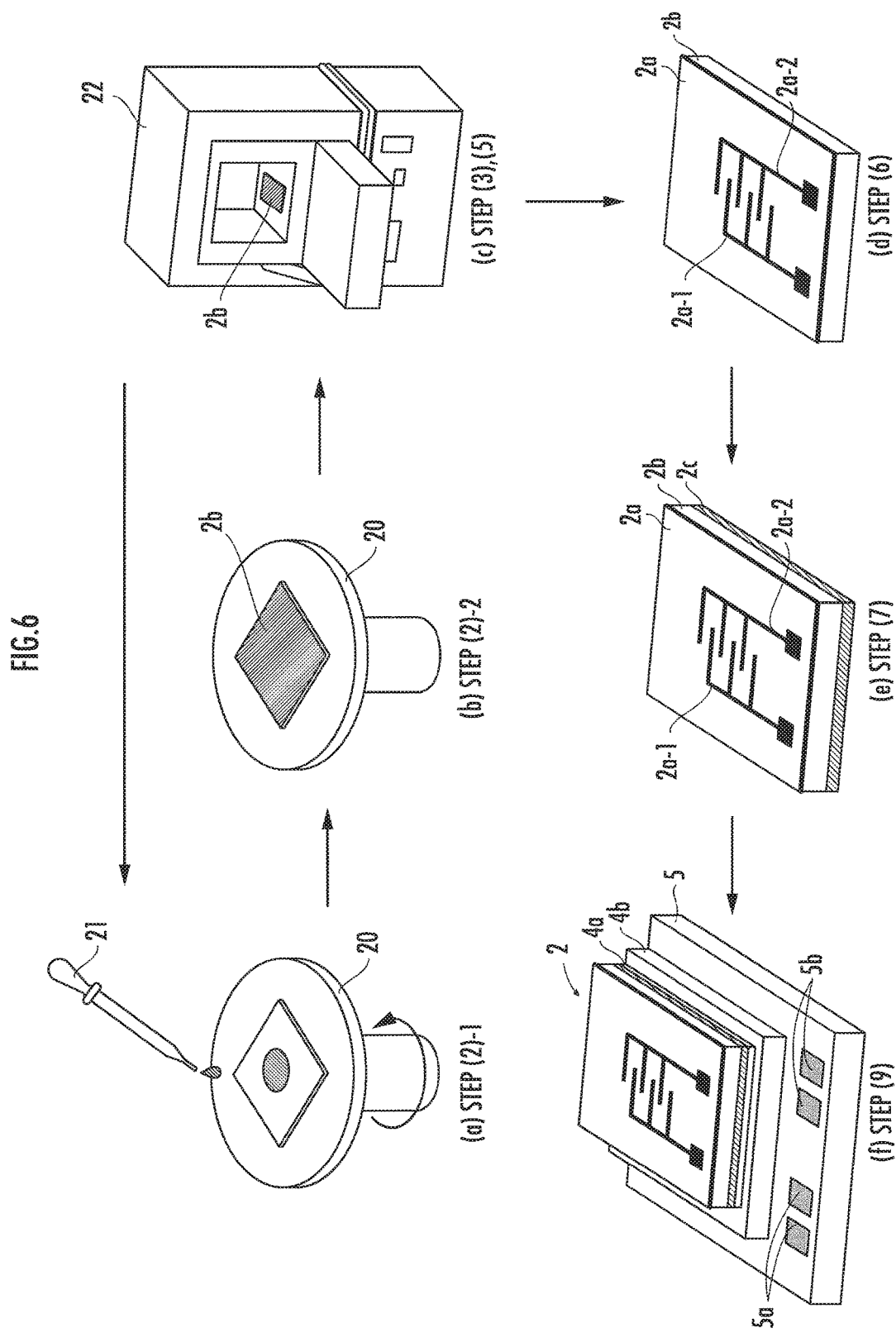

FIG.7A
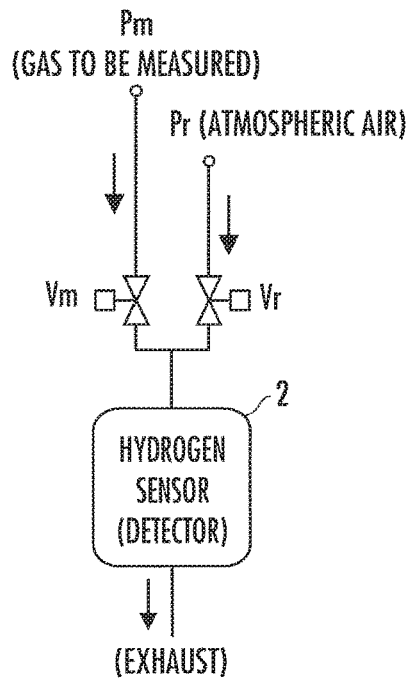
FIG.7B
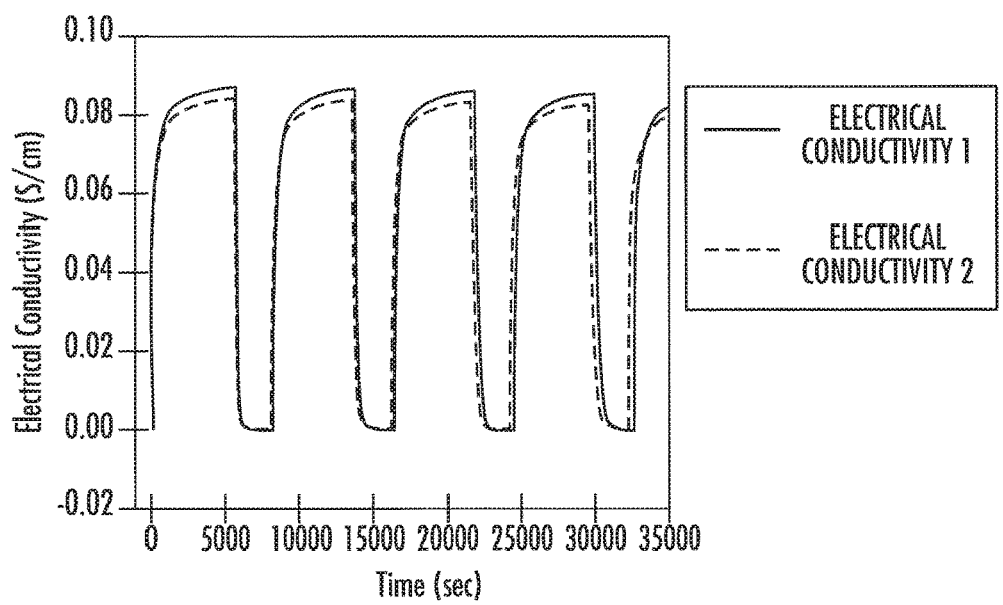
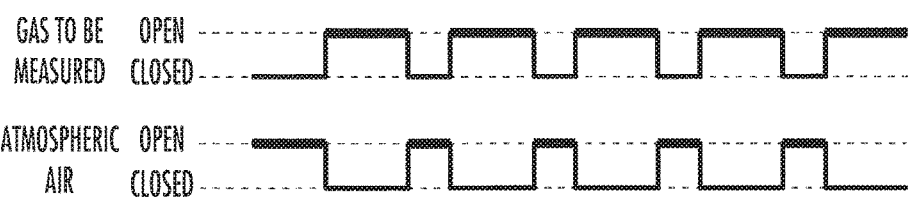

HYDROGEN CONCENTRATION MEASURING DEVICE

BACKGROUND OF THE INVENTION

Field of the Invention

The present invention relates to a hydrogen concentration measuring device adapted to measure a hydrogen concentration by using a hydrogen sensor capable of detecting hydrogen.

Description of the Related Art

Hitherto, as one type of hydrogen sensor used with a hydrogen concentration measuring device, there has been known a contact combustion type. The contact combustion type makes use of the combustion heat generated from the contact combustion of a hydrogen gas, and has a high detection sensitivity. The contact combustion type is used mainly to measure a hydrogen gas in a low concentration range of a few thousand ppm to a few ten thousand ppm.

Further, there is a method for measuring the concentration of a hydrogen gas called "the gas thermal conductivity method." This method makes use of the difference in thermal conductivity between a gas to be measured and a reference gas (e.g. atmospheric air). This method enables the measurement in an extensive concentration range from 1% to 100%, although the detection sensitivity is low.

Currently, an optical type is most typical for measuring the concentration of a hydrogen gas. For example, there has been known an optical hydrogen sensor that uses tungsten trioxide $WO_3$ or vanadium pentoxide $V_2O_5$ as a hydrogen gas sensing film.

The optical hydrogen sensor utilizes the fact that the exposure of the sensing film to a hydrogen gas changes the optical characteristics of the sensing film, thereby enabling the hydrogen gas to be detected from the attenuation of transmitted light or reflected light (optical loss). In particular, one or two layers of an alloy catalyst film (e.g. a combination of palladium Pd and rhodium Rh) are placed on the sensing film to enhance the responsiveness of the sensing film (refer to, for example, Japanese Patent Application Laid-Open No. 2007-57233).

However, the optical hydrogen sensor is known to have a relatively low detection sensitivity in a low concentration range while having a high detection sensitivity in a high concentration range. Although it is possible to perform the measurement itself in a low concentration range by the optical hydrogen sensor, there has been a problem in that the measurement in a low concentration range takes a longer time than the measurement in a high concentration range.

It could be possible to construct a hydrogen concentration measuring device capable of performing measurement in an extensive concentration range by combining different types of hydrogen sensors. However, combining different types would inconveniently make the device configuration complicated. In addition, there has been a problem in that, if there are concentration measurement values obtained by different types, then a difference in measured concentration will inconveniently occur at the time of changing the type to use.

SUMMARY OF THE INVENTION

The present invention has been made in view of the foregoing circumstances, and it is an object of the invention to provide a hydrogen concentration measuring device capable of measuring hydrogen concentrations in an extensive range with high accuracy by a simple configuration.

A hydrogen concentration measuring device in accordance with the present invention includes: a sensing film which is configured by including a metal oxide film and placed in a gas atmosphere; an electric resistance detector which detects an electric resistance of the sensing film; a transmitted light intensity detector which detects a transmitted light intensity of the sensing film; and a controller which performs first hydrogen concentration measurement processing whereby to measure a hydrogen concentration in the gas atmosphere on the basis of an electric resistance detected by the electric resistance detector in a first measurement range, second hydrogen concentration measurement processing whereby to measure the hydrogen concentration in the gas atmosphere on the basis of the transmitted light intensity detected by the transmitted light intensity detector in a second measurement range having at least a part thereof overlapping with the first measurement range, and measurement value correction processing in which processing for reducing a difference between a hydrogen concentration measured by the first hydrogen concentration measurement processing and a hydrogen concentration measured by the second hydrogen concentration measurement processing is carried out thereby to determine a measurement value of a hydrogen concentration in a range in which the first measurement range and the second measurement range overlap (a first aspect of the invention).

The electric resistance detector according to the first aspect of the invention measures a hydrogen concentration by utilizing the fact that the electric resistance of the sensing film (e.g. a metal oxide film of $Pt/WO_3$ or the like) changes when the sensing film is exposed to hydrogen. Further, the transmitted light intensity detector measures a hydrogen concentration by utilizing the fact that the intensity of light transmitted through the sensing film changes when the same sensing film is exposed to hydrogen. Hence, the device in accordance with the present invention enables a single sensing film to be used for two measurement methods, thus permitting the measurement of a hydrogen concentration by the simple configuration.

The first measurement range in which a hydrogen concentration is measured on the basis of an electric resistance and the second measurement range in which the hydrogen concentration is measured on the basis of the intensity of transmitted light overlap at least partly. Hence, there is a range in which the first hydrogen concentration measurement processing and the second hydrogen concentration measurement processing are simultaneously performed. In this case, the controller performs the measurement value correction processing whereby to reduce the difference between the hydrogen concentrations measured by the two processings to determine the measurement value of the hydrogen concentration. This enables the device in accordance with the present invention to reduce a difference between measurement values attributable to different measurement methods and to measure hydrogen concentrations with high accuracy over an extensive range.

In the first aspect of the invention, the controller calculates a weighted average value of a measurement value obtained by the first hydrogen concentration measurement processing and a measurement value obtained by the second hydrogen concentration measurement processing as the processing for reducing the difference and determines the weighted average value as the measurement value of the hydrogen concentration in the measurement value correction processing (a second aspect of the invention).

According to the second aspect of the invention, the controller calculates the weighted average value of the measurement values of the two processings to determine the hydrogen concentration in the measurement value correction processing, thus making it possible to accurately measure a hydrogen concentration that does not solely depend on the measurement value obtained by either processing. Further, the device in accordance with the present invention minimizes the possibility of the occurrence of a difference in measured concentration when changing the measurement method.

Further, in the first aspect of the invention, the controller stops the operation of the transmitted light intensity detector and measures a hydrogen concentration by the first hydrogen concentration measurement processing in the case where the hydrogen concentration is included in the first measurement range (a third aspect of the invention).

The controller in the third aspect of the invention stops the operation of the transmitted light intensity detector if a hydrogen concentration is included in the first measurement range. Hence, the device in accordance with the present invention measures the hydrogen concentration by the first hydrogen concentration measurement processing without performing the second hydrogen concentration measurement processing. This enables a power-saving hydrogen concentration measuring device to be achieved.

Further, in the second aspect of the invention, the controller may stop the operation of the transmitted light intensity detector and measure a hydrogen concentration by the first hydrogen concentration measurement processing in the case where the hydrogen concentration is included in the first measurement range.

Further, in the first aspect of the invention, the hydrogen concentration measuring device includes a light amount recognizing unit which recognizes the light amount of a light source, wherein the transmitted light intensity detector re-sets a reference value of the light amount in the case where an increase or a decrease in the light amount is recognized by the light amount recognizing unit (a fourth aspect of the invention).

The light amount of a light source used for detecting the intensity of transmitted light changes in some cases due to deterioration or a usage environment. Taking this into account, the hydrogen concentration measuring device in accordance with the present invention includes the light amount recognizing unit, which re-sets the reference value of the light amount in the case where an increase or a decrease in the light amount is recognized. This arrangement enables the device in accordance with the present invention to always detect an accurate intensity of transmitted light.

In the second aspect of the invention, the hydrogen concentration measuring device may include a light amount recognizing unit that recognizes the light amount of a light source, and the transmitted light intensity detector may re-set the reference value of the light amount in the case where an increase or a decrease in the light amount is recognized by the light amount recognizing unit.

Further, in the third aspect of the invention, the hydrogen concentration measuring device may include a light amount recognizing unit which recognizes the light amount of a light source, and the transmitted light intensity detector may re-set the reference value of the light amount in the case where an increase or a decrease in the light amount is recognized by the light amount recognizing unit.

Further, in the first aspect of the invention, the hydrogen concentration measuring device includes a reset gas feeder which sends out a reset gas for resetting a hydrogen concentration to the sensing film, wherein the controller actuates the reset gas feeder in the case where a hydrogen gas concentration is measured in a non-oxidizing gas atmosphere (a fifth aspect of the invention).

The sensing film according to the fifth aspect of the invention is characterized in that, in a non-oxidizing gas atmosphere which does not contain oxygen, the sensing film retains the conditions (the electric resistance value and the light transmission rate of the sensing film) obtained by its first exposure to hydrogen and will not be reset. Hence, when measuring the hydrogen gas concentration in the non-oxidizing gas atmosphere, the reset gas feeder is actuated to send out the reset gas to the sensing film thereby to reset the sensing film to the initial condition thereof. This arrangement enables the device in accordance with the present invention to accurately measure a hydrogen concentration also in the non-oxidizing gas atmosphere.

Further, in the second aspect of the invention, the hydrogen concentration measuring device may include a reset gas feeder which sends out a reset gas for resetting a hydrogen concentration to the sensing film, and the controller may actuate the reset gas feeder in the case where a hydrogen gas concentration is measured in a non-oxidizing gas atmosphere.

Further, in the third aspect of the invention, the hydrogen concentration measuring device may include a reset gas feeder which sends out a reset gas for resetting a hydrogen concentration to the sensing film, and the controller may actuate the reset gas feeder in the case where a hydrogen gas concentration is measured in a non-oxidizing gas atmosphere.

Further, in the fourth aspect of the invention, the hydrogen concentration measuring device may include a reset gas feeder which sends out a reset gas for resetting a hydrogen concentration to the sensing film, and the controller may actuate the reset gas feeder in the case where a hydrogen gas concentration is measured in a non-oxidizing gas atmosphere.

BRIEF DESCRIPTION OF THE DRAWINGS

FIG. 5B is a control flowchart of the hydrogen concentration measuring device (Modified example 2);

FIG. 6 is a diagram illustrating the fabrication method of the hydrogen sensor and the method of mounting the hydrogen sensor on a substrate;

FIG. 7A is a diagram illustrating the device configuration applied to measure a hydrogen concentration in a non-oxidizing gas atmosphere;

FIG. 7B illustrates an example of the measurement of a hydrogen concentration in a non-oxidizing gas atmosphere;

DESCRIPTION OF THE PREFERRED EMBODIMENTS

First Embodiment

Figure 1:
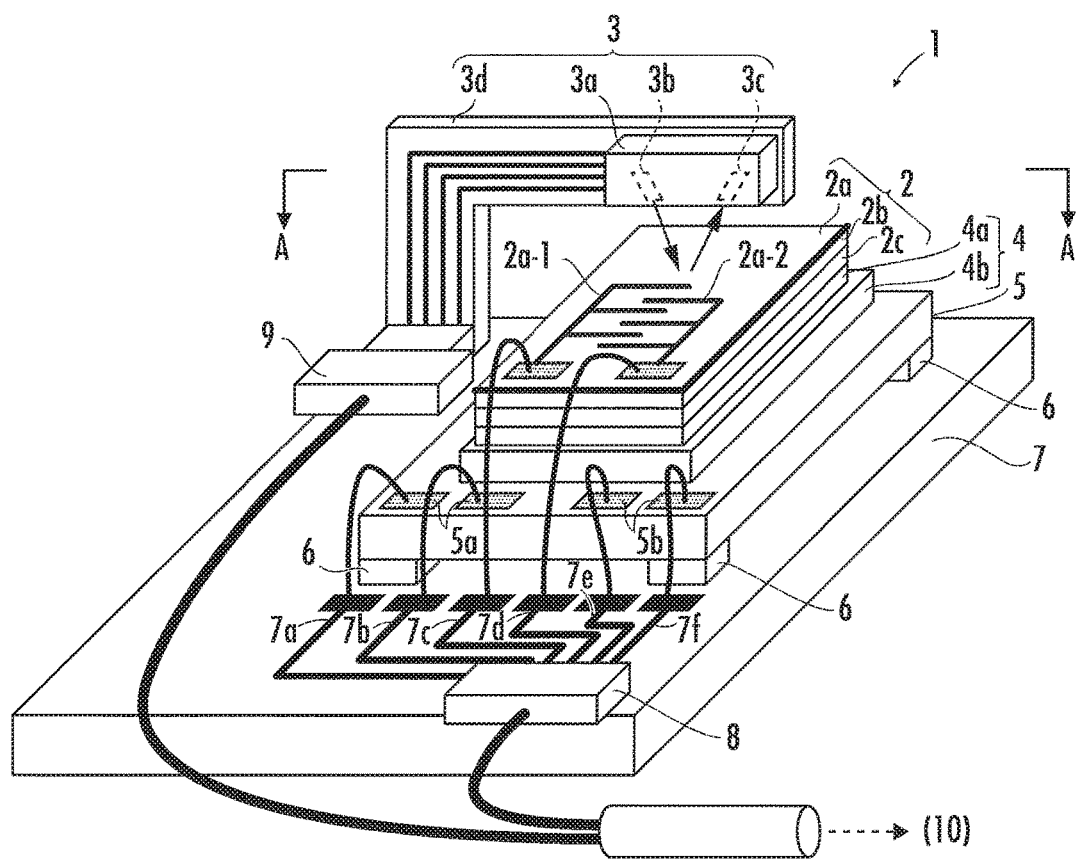
FIG. 1 is a configuration diagram of a hydrogen sensor of a first embodiment of a hydrogen concentration measuring device.

FIG. 1 illustrates the configuration of the hydrogen concentration measuring device (composed primarily of a hydrogen sensor) in accordance with the present invention.

A hydrogen concentration measuring device 1 is capable of measuring a hydrogen concentration by two methods, namely, a measurement method based on electric resistance and a measurement method based on the intensity of transmitted light. The hydrogen concentration measuring device 1 is comprised mainly of a sensor chip 2 (composed of 2a to 2c), an optical measurement unit 3 (composed of 3a to 3d), and a heater 5. These members are mounted on a substrate 7.

The sensing film 2a is formed on an uppermost layer of the sensor chip 2. The sensor chip 2 is used for both the electric resistance measurement and the transmitted light intensity measurement. The sensing film 2a is a thin film (Pt/WO$_3$ film) composed of platinum (Pt) and tungsten trioxide WO$_3$ (the metal oxide film in the present invention) and is formed on an upper layer of the light-transmissive substrate 2b. A pair of comb-shaped electrodes 2a-1 and 2a-2 are provided on the surface of sensing film 2a and connected to an electrical measurement connector 8 by wires and electrical measurement lines 7c and 7d on the substrate 7.

The optical measurement member package 3a of the optical measurement unit 3 is comprised of the light source 3b, which outputs observation light to the sensor chip 2, and the light receiving element 3c, which detects the reflected light from the sensor chip 2, and is used only for measuring the transmitted light intensity of a hydrogen concentration. The light source 3b and the light receiving element 3c are connected to an optical measurement connector 9 through the wiring on the optical measurement stay 3d.

The heater 5 is joined to the sensor chip 2 through a joining part 4 (composed of 4a and 4b). The sensitivity of the sensing film 2a may deteriorate due to the influence of humidity, so that the temperature of the sensor chip 2 is maintained at, for example, 60° C. or more, at which there will hardly be the influence of humidity. Keeping warm also provides effect for expediting a chemical reaction, which will be discussed hereinafter.

The heater 5 may be any type of heater insofar as the performance thereof enables the heater to reach a desired temperature in a few seconds. Preferably, however, the heater 5 is a compact ceramic heater or a Micro Electro Mechanical Systems (MEMS) heater.

The heater 5 is placed on the substrate 7 through the intermediary of four spacers 6 provided on the substrate 7. With this arrangement, the substrate 7 will be hardly subjected to the influence of heat even when the temperature of the heater 5 becomes high. Placed on the upper surface of the heater 5 are heating power terminals 5a and temperature measuring element terminals 5b, which are connected by wires to electrical measurement lines 7a, 7b on the substrate 7 and electrical measurement lines 7e, 7f and further to the electrical measurement connector 8.

A brief description will now be given of the principle of the electric resistance measurement of the hydrogen concentration measuring device 1.

The Pt atoms of the sensing film 2a (Pt/WO$_3$ film) are scattered everywhere in the WO$_3$ film. Further, when the sensing film 2a is exposed to hydrogen, hydrogen molecules H$_2$ are atomized at the surface of Pt and diffused into the WO$_3$ film (spill-over effect). Further, the hydrogen H is ionized so as to exist in the form of protons H$^+$ and electrons e$^-$. This phenomenon is indicated by a chemical reaction formula given below.

$$H_2 \rightarrow 2H^+ + 2e^- \qquad \text{(Chemical reaction formula 1)}$$

Further, a part of tungsten ions W$^{6+}$ in the WO$_3$ firm changes into W$^{5+}$ and forms a light absorption band in a visible light region. This causes the electrons e$^-$ to become carriers, expediting electrical conduction. At this time, a chemical reaction formula given below applies, M$^+$ being a monovalent cation.

$$WO_3 + xM^+ + xe^- \leftrightarrows M_xWO_3 \qquad \text{(Chemical reaction formula 2)}$$

This means that the carrier concentration of the sensing film 2a increases in proportion to the hydrogen concentration. The hydrogen concentration measuring device 1 can measure the hydrogen concentration by measuring the electric resistance between the electrodes by the comb-shaped electrodes 2a-1 and 2a-2 of the sensing film 2a. The sensor chip 2, which includes the sensing film 2a and the comb-shaped electrodes 2a-1 and 2a-2, corresponds to the electric resistance detector in the present invention.

More specifically, the electric resistance of the sensing film 2a is high in the case where there is no hydrogen in a gas to be measured. When the hydrogen concentration in a gas reaches the range from 500 ppm to 1000 ppm, the electric resistance starts to decrease, and the decrease in the electric resistance ceases when the hydrogen concentration reaches a level of a few percent. The electric resistance measurement is performed mainly to measure a hydrogen concentration in a low concentration ranging from about 500 ppm (0.05%) to about 4.0%.

Although the electric resistance measurement can be applied to a hydrogen concentration of 4.0% or more, the response time will be disadvantageously longer. The measurement values of the electric resistance measurement are sent eventually to a measurement unit 10 from the electrical measurement connector 8.

A brief description will now be given of the principle of the transmitted light intensity measurement of the hydrogen concentration measuring device 1.

It has been described above that the sensing film 2a forms the light absorption band when a part of the tungsten ions W$^{6+}$ in the WO$_3$ film changes to W$^{5+}$. More specifically, near-infrared light is absorbed from red light, causing the sensing film 2a to be colored blue.

The coloring of the sensing film 2a of the sensor chip 2 is weak when the hydrogen concentration in a gas atmosphere is low, and becomes stronger as the hydrogen concentration increases. Hence, the hydrogen concentration measuring device 1 can measure the hydrogen concentration by measuring the intensity of the observation light when the observation light enters the light receiving element 3c (e.g. a photodiode) after being output from the light source 3b (e.g. a light-emitting diode or a laser diode), transmitted through the sensing film 2a and the light-transmissive substrate 2b, reflected off of the reflection film 2c and then transmitted through the sensing film 2a and the light-transmissive substrate 2b again. The sensor chip 2, which includes the sensing film 2a, and the optical measurement unit 3, which includes the light source 3b and the light receiving element 3c, correspond to the transmitted light intensity detector in the present invention.

If the sensing film 2a is a Pt/WO$_3$ film, then a light source capable of outputting observation light having a wavelength of 600 nm to 900 nm is used. The wavelength of the observation light can be selected according to the type of the sensing film.

Further, in an atmosphere containing oxygen, the hydrogen H diffused in the sensing film 2a reacts with oxygen O$_2$, producing water. With platinum Pt as the catalyst, a chemical reaction expressed by the following formula will take place.

$$2H^+ + 2e^- + 1/2O_2 \rightarrow H_2O \qquad \text{(Chemical reaction formula 3)}$$

Thus, the hydrogen H in the sensing film 2a desorbs, causing the sensing film 2a to be decolored (made transparent).

The transmitted light intensity measurement can be applied to a hydrogen concentration mainly in an extensive measurement range of 1.0% to 100%. Although the transmitted light intensity measurement can be applied to a hydrogen concentration in a range of 1.0% or less, the response time will be disadvantageously longer.

In the atmosphere, since the concentration of oxygen is stabilized at approximately 20%, the electric resistance and the light transmission rate increases or decreases according to a change in the concentration of hydrogen. This is true with both the electric resistance measurement and the transmitted light intensity measurement. However, caution is required, because the hydrogen concentration is inconveniently influenced by oxygen in an atmosphere in which the oxygen concentration increases or decreases.

Figure 2:
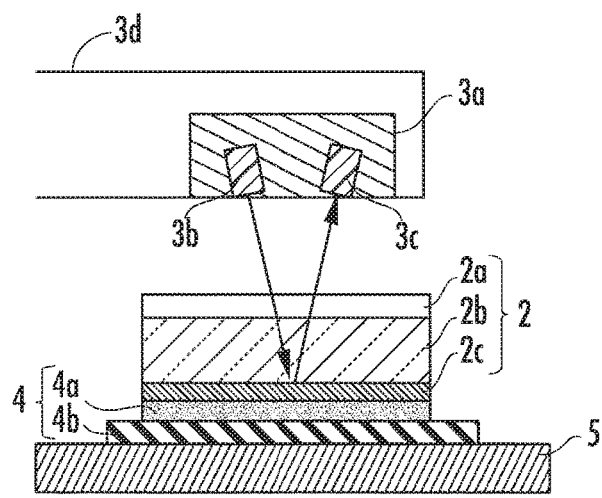
FIG. 2 is a sectional view taken along line A-A of the hydrogen sensor in FIG. 1.

FIG. 2 is a sectional view of the sensor chip 2 and the optical measurement unit 3. In reality, the spacers 6 and the substrate 7 are included, but these components are not illustrated here.

First, the sensor chip 2 has a layered structure, in which the sensing film 2a, the light-transmissive substrate 2b, and the reflection film 2c are deposited in this order from the top. The observation light output from the light source 3b of the optical measurement member package 3a passes through the sensing film 2a and the light-transmissive substrate 2b and is reflected off of the reflection film 2c composed of a metal film made of silver, aluminum or the like.

Then, the light reflected off of the reflection film 2c is received by the light receiving element 3c of the optical measurement member package 3a. Although not illustrated, the light source 3b is provided with a collimating lens for turning the observation light into a parallel beam, and the light receiving element 3c is provided with a condenser lens. This arrangement enables the reflected light to efficiently enter the light receiving element 3c.

The joining member 4a is a member for joining the reflection film 2c and the joining pad 4b on the upper surface of the heater 5 (the details of which will be discussed hereinafter). The joining member 4a and the joining pad 4b are preferably made of a material that has high thermal conductivity to permit easy heat transfer from the heater 5.

As a second embodiment, there is a method in which the reflection film 2c is not provided, and the observation light is output from a light source disposed above the sensing film 2a and the transmitted light is detected by a light receiving element disposed below the light-transmissive substrate 2b.

A description will now be given of the control of the hydrogen concentration measuring device 1 with reference to FIG. 3A and FIG. 3B.

Figure 3A:
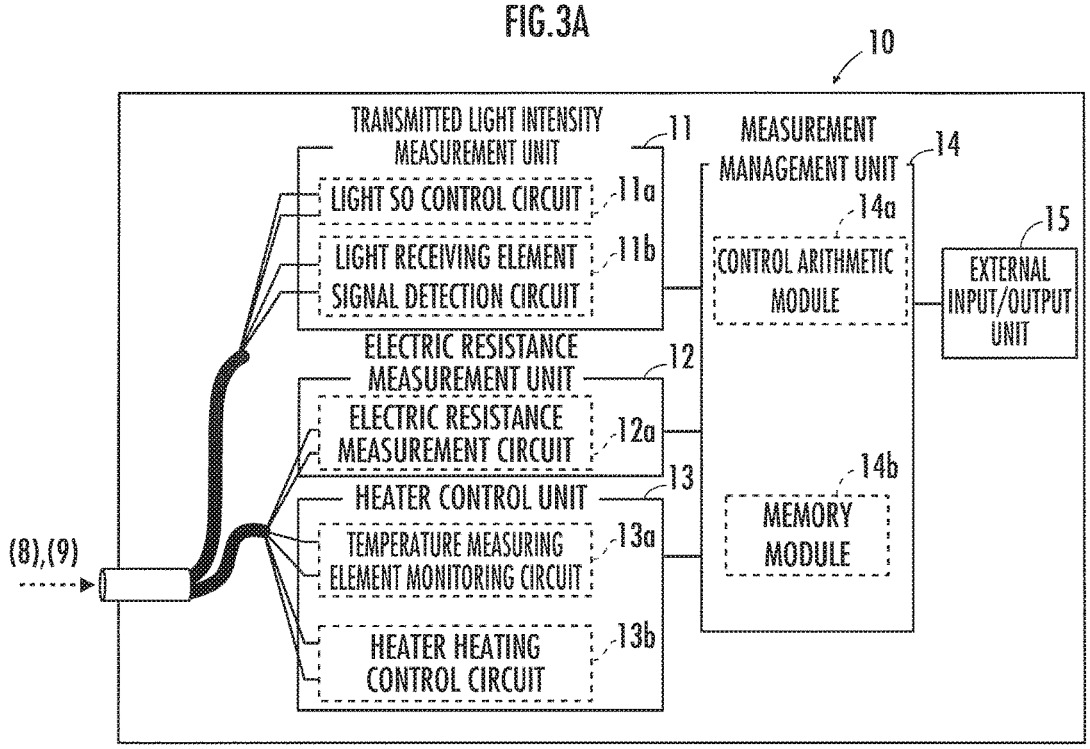
FIG. 3A is a block diagram of a measuring unit of the hydrogen concentration measuring device.

FIG. 3A illustrates the configuration of the measurement unit 10 of the hydrogen concentration measuring device 1. The measurement unit 10 is comprised of a transmitted light intensity measurement unit 11 which measures the transmitted light intensity of the sensing film 2a, an electric resistance measurement unit 12 which measures the electric resistance of the sensing film 2a, a heater control unit 13 which heats the sensing film 2a at a fixed temperature by the heater 5 to improve measurement accuracy, a measurement management unit 14 which integrally manages the measurement values of each unit, and an external input/output unit 15 which communicates with external equipment.

The transmitted light intensity measurement unit 11 is comprised of a light source control circuit 11a and a light receiving element signal detection circuit 11b. The light source control circuit 11a controls the light source 3b to emit the observation light of a predetermined amount of light to the sensing film 2a. Further, the light receiving element signal detection circuit 11b receives a signal of the light receiving element 3c which has received the reflected light from the sensing film 2a. Thus, a change M absorbance A by the coloring of the sensing film 2a is detected.

If the intensity of transmitted light is denoted by I and the intensity of incident light is denoted by I$_0$ (the intensity of transmitted light when the sensing film 2a is transparent), then absorbance A is given according to the following expression.

$$A = -\log_{10}(I/I_0) \qquad \text{(Expression 1)}$$

The electric resistance measurement unit 12 is composed of an electric resistance measurement circuit 12a. The electric resistance measurement circuit 12a measures a change in the electric resistance of the sensing film 2a by a change in electric conductivity σ. If the resistivity is denoted by ρ, then the electric conductivity σ is given by the following expression.

$$\sigma = 1/\rho \qquad \text{(Expression 2)}$$

Further, the relationship among the resistivity ρ, an electric resistance R, the length of wiring L, and a sectional area S is represented by the following formula.

$$R = \rho(L/S) \qquad \text{(Expression 3)}$$

More specifically, a Wheatstone bridge circuit including the sensor chip 2 is incorporated to make adjustment such that the bridge circuit is placed in a balanced state in the absence of hydrogen. With this arrangement, when the balanced state is disturbed, a change in the electric resistance can be detected.

The heater control unit 13 is comprised of a temperature measuring element monitoring circuit 13a and a heater heating control circuit 13b. The temperature measuring element monitoring circuit 13a observes the temperature of the heater 5 on the basis of a signal transmitted from a temperature measuring element terminal 5b on the heater 5. Further, the heater heating control circuit 13b performs control to maintain the sensor chip 2 at a predetermined temperature (normally 120° C.) between 60° C. and 300° C. in order to enable stable measurement of a hydrogen concentration without being influenced by an atmospheric temperature or a change in the humidity of a gas to be measured.

The measurement management unit 14 is comprised of a control arithmetic module 14a and a memory module 14b. The control arithmetic module 14a outputs a required instruction to each unit and receives various types of signals required to calculate a hydrogen concentration according to instructions from the external input/output unit 15. Further, the control arithmetic module 14a compares the values of the electric conductivity σ or absorbance A, which will provide a calibration curve stored in the memory module 14b, with measurement values thereby to determine a hydrogen concentration, and outputs necessary information to the external input/output unit 15.

The external input/output unit 15 has an interface for communicating necessary information with external equipment. For example, a communication specification of RS232C, RS485, GP-W, CC-link, DeviceNet, C contact, LAN interface or the like can be used. Alternatively, the measurement unit 10 may be provided with various switches and a concentration display unit, which are to be directly operated.

Figure 3B:
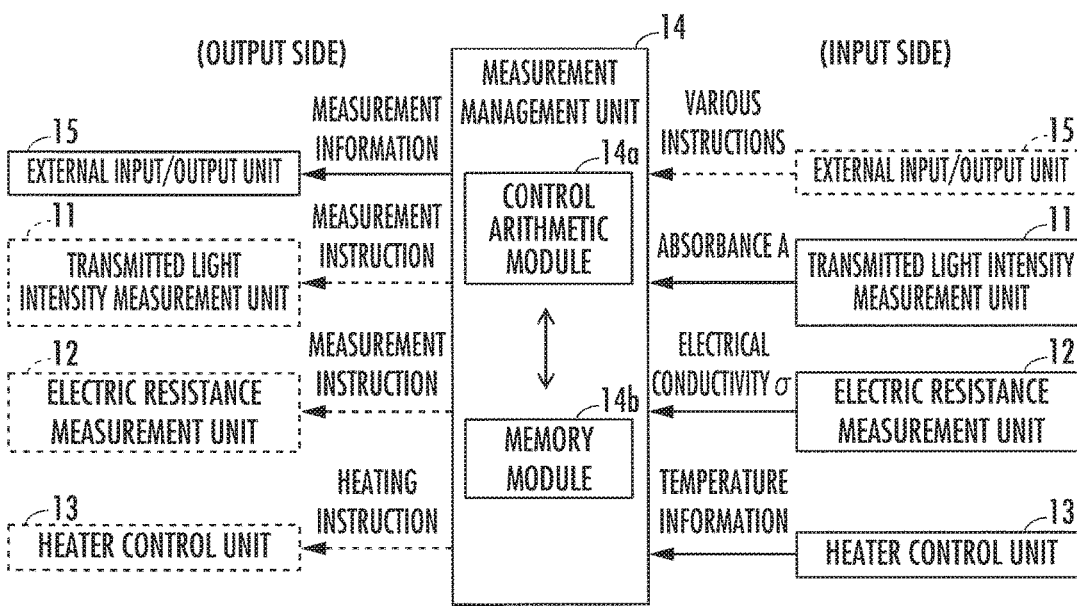
FIG. 3B is a diagram illustrating the control system of the hydrogen concentration measuring device.

FIG. 3B illustrates the control system of the hydrogen concentration measuring device 1.

In the hydrogen concentration measuring device 1, inputs and outputs are performed, centering around the measurement management unit 14. Basically, instructions are received from the external input/output unit 15 on the input side, and the instructions are issued to the units on the output side. Further, the information of each unit on the input side is sent as measurement information to the external equipment (the light source 3b, the heater 5 and the like) through the intermediary of the measurement management unit 14 and the external input/output unit 15 on the output side.

For example, if a measurement instruction is issued from the external input/output unit 15, then a heating instruction is issued to the heater control unit 13 through the intermediary of the measurement management unit 14. Then, when a predetermined temperature (e.g. 120° C.) is reached after the heater control unit 13 starts heating of the heater 5, a status indicating that the temperature has been reached is returned.

Further, if the external input/output unit 15 issues the measurement instruction to the transmitted light intensity measurement unit 11 through the intermediary of the measurement management unit 14, then the transmitted light intensity measurement unit 11 causes the light source 3b to emit light, the light receiving element 3c to receive the reflected light, and returns the value of absorbance A at predetermined intervals. Similarly, if the external input/output unit 15 issues the measurement instruction to the electric resistance measurement unit 12 through the intermediary of the measurement management unit 14, then the electric resistance measurement unit 12 returns the value of the electric conductivity σ at predetermined intervals.

The control arithmetic module 14a of the measurement management unit 14 compares the measurement values returned from the transmitted light intensity measurement unit 11 and the electric resistance measurement unit 12 with the calibration curve values stored in the memory module 14b to determine the accuracy, and outputs a proper value of the hydrogen concentration to the external input/output unit 15.

In addition to the foregoing instructions, a variety of other instructions, including an electric resistance measurement instruction for measuring a hydrogen concentration only on the basis of the electric conductivity σ and a transmitted light intensity measurement instruction for measuring a hydrogen concentration only on the basis of absorbance A, and a heater heating instruction for actuating only the heater 5, can be issued.

Figure 4:
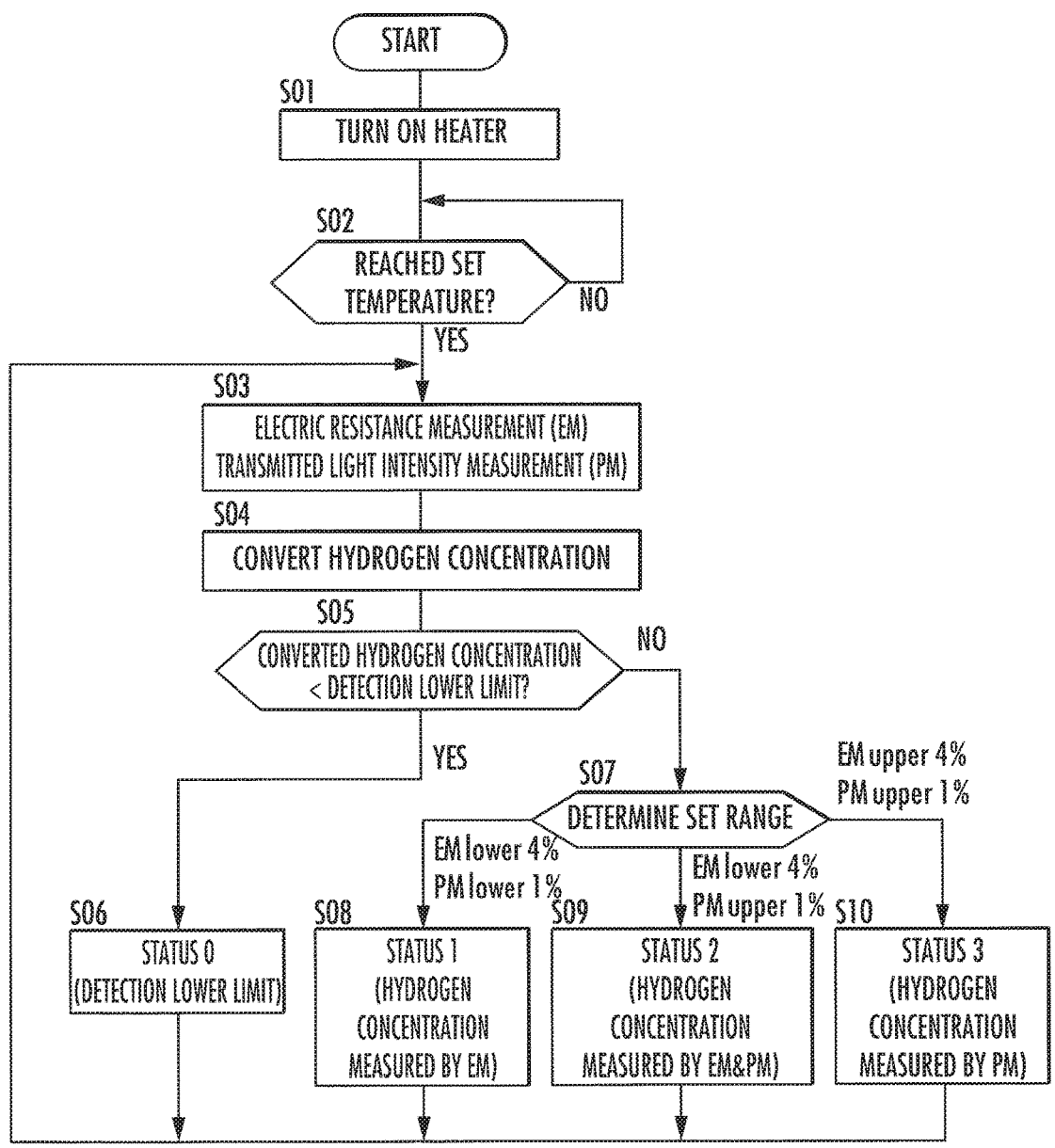
FIG. 4 is a control flowchart of the hydrogen concentration measuring device.

Referring now to FIG. 4, the control flow of the hydrogen concentration measuring device 1 when a hydrogen concentration is measured will be described.

When the measurement instruction is issued from the external input/output unit 15, the control unit (the control arithmetic module 14a) of the hydrogen concentration measuring device 1 begins the measurement of a hydrogen concentration. First, the control unit turns on the heater (step S01). More specifically, the control unit turns on the temperature measuring element monitoring circuit 13a and the heater heating control circuit 13b of the heater control unit 13 to start heating the sensor chip 2 by the heater 5, and also starts feedback control. Thereafter, the control unit proceeds to step S02.

Then, the control unit determines whether a set temperature is reached (step S02). For example, if the temperature has been set to 120° C., then until 120° C. is reached, the determination result will be "NO" and the step S02 is repeated. When the temperature reaches 120° C., the control unit proceeds to step S03.

When the set temperature is reached ("YES" in step S02), the control unit starts the electric resistance measurement (EM: Electric Measurement) and the transmitted light intensity measurement (PM: Photometer Measurement) (step S03). More specifically, the control unit turns on the light source control circuit 11a and the light receiving element signal detection circuit 11b of the transmitted light intensity measurement unit 11 to detect absorbance A. At the same time, the control unit turns on the electric resistance measurement circuit 12a of the electric resistance measurement unit 12 to calculate the electric conductivity σ from the electric resistance R. Thereafter, the control unit proceeds to step S04.

Subsequently, the control unit performs conversion of the hydrogen concentration (step S04). More specifically, the control unit compares the values of the electric conductivity σ or absorbance A, which are the calibration curves stored in the memory module 14b of the measurement management unit 14, with the current measurement values. Then, the control unit calculates the hydrogen concentrations of the electric resistance measurement (EM) and the transmitted light intensity measurement (PM). Thereafter, the control unit proceeds to step S05.

Subsequently; the control unit determines a detection lower limit (step S05). If the hydrogen concentrations obtained by both measurement methods are below the detection lower limit (e.g. 0.05%), then the control unit proceeds to step S06. Meanwhile, if hydrogen of a concentration equal to or more than the detection lower limit is detected, then the control unit proceeds to step S07.

If the hydrogen concentrations are below the detection lower limit ("YES" in step S05), then the control unit sets "status 0" (step S06). The "status 0" indicates that the hydrogen concentration is extremely low and there is not a danger of explosion or the like caused by hydrogen. Thereafter, the control unit returns to step S03 and repeats the process from step S03 to step S05.

Meanwhile, if hydrogen of a concentration equal to or more than the detection lower limit is detected ("NO" in step S05), then the control unit determines a set range (step S07). If the determination result indicates below 4% in terms of the electric resistance measurement (EM) and below 1% in terms of the transmitted light intensity measurement (PM), then the control unit sets "status 1" (step S08). At this time, the hydrogen concentration of the electric resistance measurement (EM) is adopted.

Further, if the determination result indicates below 4% in terms of the electric resistance measurement (EM) and 1% or more in terms of the transmitted light intensity measurement (PM), then the control unit sets "status 2" (step S09). At this time, the hydrogen concentrations obtained by both measurement methods are adopted.

More specifically, the control unit calculates the weighted average value of the measurement values of both the electric resistance measurement (EM) and the transmitted light intensity measurement (PM) and determines the weighted average value as the measurement value of the hydrogen concentration (the measurement value correction processing in the present invention). For example, if the hydrogen concentration is 1%, then the sensitivity in the electric resistance measurement (EM) is high, while the sensitivity in the transmitted light intensity measurement (PM) is low. Therefore, the control unit adds a great weight (e.g. 0.8) to the measurement value of the electric resistance measurement (EM) and a small weight (e.g. 0.2) to the measurement value of the transmitted light intensity measurement (PM), and calculates the sum of the two measurement values. The calculated value is the weighted average value in the case where the hydrogen concentration is 1%.

Meanwhile, if the hydrogen concentration is close to 4%, then the sensitivity in the transmitted light intensity measurement (PM) is high, while the sensitivity in the electric resistance measurement (EM) is low. Therefore, the control unit adds a great weight (e.g. 0.8) to the measurement value of the transmitted light intensity measurement (PM) and a small weight (e.g. 0.2) to the measurement value of the electric resistance measurement (EM), and calculates the sum of the two measurement values.

Thus, the control unit calculates the weighted average value of both measurement values in the overlapped measurement range (the overlapped range in the present invention), in which a hydrogen concentration is measured by both measurement methods. This arrangement minimizes the possibility of occurrence of a difference in measured concentration when a hydrogen concentration gradually increases and the concentration range is switched from the overlapped measurement range to the transmitted light intensity measurement (PM) range. Thereafter, the control unit returns to step S03.

Finally, if the electric resistance measurement (EM) result indicates 4% or more and the transmitted light intensity measurement (PM) result indicates 1% or more, then the control unit sets "status 3" (step S10). In this case, the hydrogen concentration obtained by the transmitted light intensity measurement (PM) is adopted. Thereafter, the control unit returns to step S03.

If an interference gas (hydrogen sulfide $H_2S$, nitric monoxide NO, ammonia $NH_3$ or the like) infiltrates into a gas atmosphere, then the interference gas will be also detected in the electric resistance measurement (EM), undesirably leading to the occurrence of an error in a hydrogen concentration. Meanwhile, an interference gas will not be detected at all in the transmitted light intensity measurement (PM). Hence, in the foregoing "status 2," if a measurement value of the electric resistance measurement (EM) is different from a measurement value of the transmitted light intensity measurement (PM) by a predetermined amount (e.g. 10%) or more, then preferably, the measurement value of the electric resistance measurement (EM) is corrected, considering the presence of an interference gas, and the corrected value is used, or only the measurement value of the transmitted light intensity measurement (PM) is used.

Further, the same can be applied to the case where an interference gas infiltrates into an atmosphere in the "status 1." In the "status 1," the measurement itself can be performed although the response time in the transmitted light intensity measurement (PM) will be slightly longer than usual. Accordingly, the measurement value of the electric resistance measurement (EM) may be corrected and the corrected value may be used, or only the measurement value of the transmitted light intensity measurement (PM) may be used.

Figure 5A:
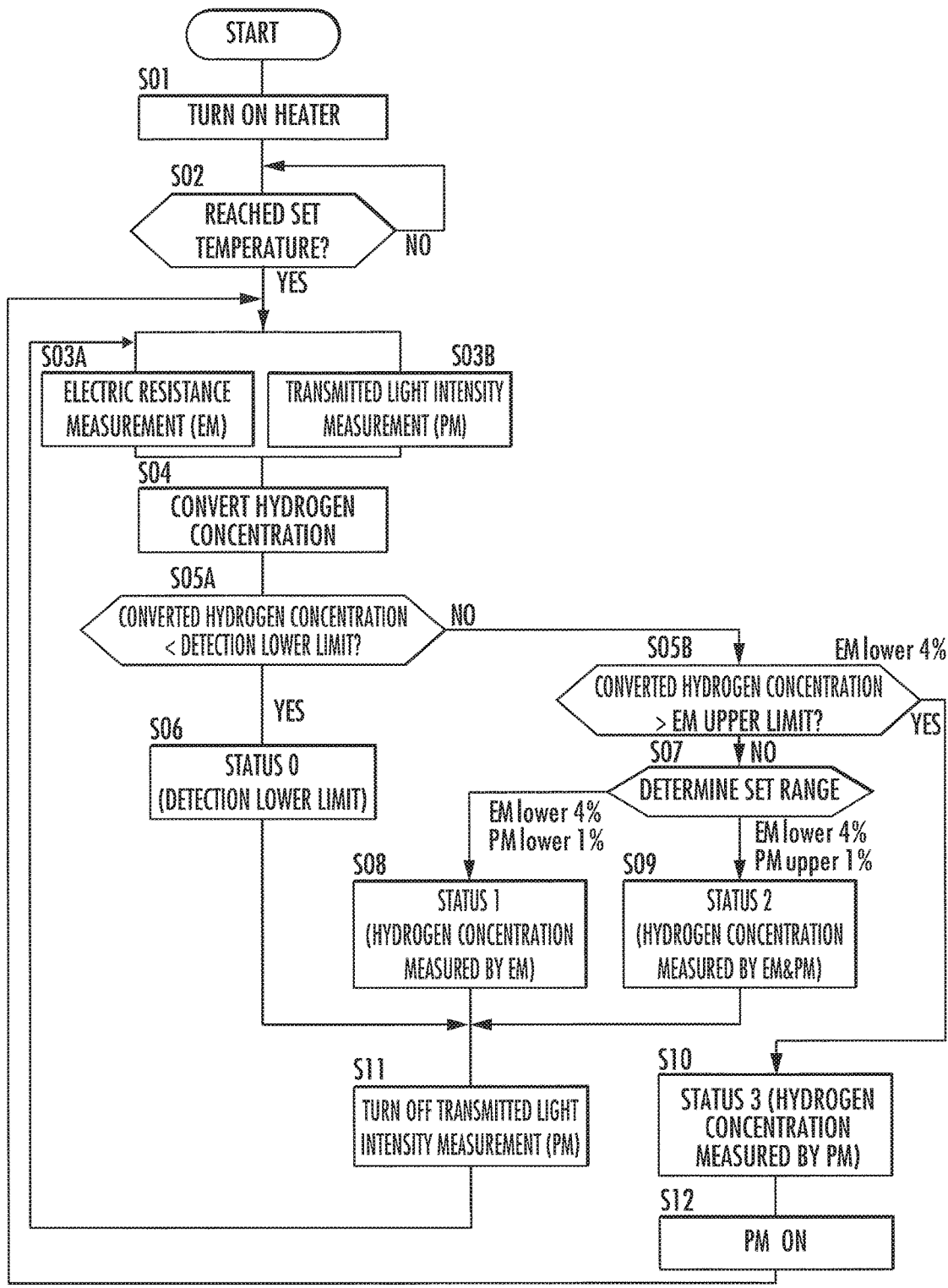
FIG. 5A is a control flowchart of the hydrogen concentration measuring device (Modified example 1)

Referring now to FIG. 5A and FIG. 5B, a description will be given of a modified example of the control flow of the hydrogen concentration measuring device 1 when measuring a hydrogen concentration.

First, FIG. 5A illustrates the control flow of stopping the transmitted light intensity measurement (PM) when a predetermined condition is satisfied and measuring a hydrogen concentration only by the electric resistance measurement (EM). Steps S01 and S02 are the same as those of the control flow in FIG. 4, so that the description thereof will be omitted.

When a set temperature is reached (YES in step S02), the control unit performs the electric resistance measurement (EM) in step S03A and the transmitted light intensity measurement (PM) in step S03B. The details of the measurements are the same as the measurements in the control flow in FIG. 4, but the step has been divided for the subsequent processing. Thereafter, the control unit proceeds to step S05A via step S04.

In step S05A, the control unit determines the detection lower limit. If the measurement results of the hydrogen concentration obtained by the two measurement methods are below the detection lower limit, then the control unit proceeds to step S06. Meanwhile, if the measurement results of the hydrogen concentration obtained by the two measurement methods are equal to or more than the detection lower limit, then the control unit proceeds to step S05B.

If the hydrogen concentration is below the detection lower limit (YES in step S05A), then the control unit sets the "status 0." This means a state below the detection lower limit, indicating that there is no danger of an explosion or the like caused by hydrogen. Thereafter, the control unit proceeds to step S11.

On the other hand, if hydrogen equal to or more than the detection lower limit is detected (NO in step S05A), then the control unit determines an EM upper limit (step S05B). In other words, the control unit determines whether hydrogen equal to or more than the upper limit of the electric resistance measurement (EM) has been detected. If the EM upper limit is exceeded, the control unit proceeds to step S10. Meanwhile, if the detected hydrogen is below the EM upper limit, then the control unit proceeds to step S07.

If the detected hydrogen is below the EM upper limit (NO in step S05B), then the control unit determines a set range (step S07). If the determination result indicates below 4% in terms of the electric resistance measurement (EM) and below 1% in terms of the transmitted light intensity measurement (PM), then the control unit sets the "status 1" (step S08). At this time, the hydrogen concentration of the electric resistance measurement (EM) is adopted, Thereafter, the control unit proceeds to step S11.

If the determination result indicates below 4% in terms of the electric resistance measurement (EM) and 1% or more in terms of the transmitted light intensity measurement (PM), then the control unit sets the "status 2" (step S09). At this time, the hydrogen concentrations of the two measurement methods are adopted only for a first loop, but thereafter, the hydrogen concentration obtained by the electric resistance measurement (EM) is adopted for the processing in step S11, which will be discussed hereinafter. After that, the control unit proceeds to step S11.

In step S11, the control unit turns off the transmitted light intensity measurement (PM). In other words, during the period in which "status 0" to "status 2" are set, the hydrogen concentration is measured only by the electric resistance measurement (EM). Comparison with the control flow in FIG. 4 indicates that no measurement is performed using both measurement methods in a range in which the hydrogen concentration is 1% to 4% except for some cases. This means an energy-saving control flow. Thereafter, the control unit returns to step S03A.

Next, if hydrogen at a concentration equal to or more than the EM upper limit is detected (YES in step S05B), then the control unit sets a "status 3" (step S10). Thereafter, the control unit proceeds to step S12.

In step S12, the control unit turns on the transmitted light intensity measurement (PM). In a situation in which the hydrogen concentration gradually increases, the hydrogen concentration has been so far measured using only the electric resistance measurement (EM). In the present step, it is prepared for starting the transmitted light intensity measurement (PM). Thereafter, the control unit returns to steps S03A and S03B.

If the hydrogen concentration is equal to or more than the EM upper limit, then the measurement itself can be performed, although the response time of the electric resistance measurement (EM) will be slightly longer than usual. Hence, for a predetermined concentration range, the hydrogen concentration will be measured by both the electric resistance measurement (EM) method and the transmitted light intensity measurement (PM) method. However, the electric resistance measurement (EM) will eventually stop responding, so that a measurement value of the transmitted light intensity measurement (PM) will be adopted.

For the range in which the hydrogen concentration is detected by both measurement methods, the weighted average value of the measurement values obtained by both measurement methods may be used to calculate the hydrogen concentration, as with the control flow in FIG. 4. This makes it possible to reduce the difference in concentration that occurs when changing the measurement method.

FIG. 5B illustrates the control whereby to correct an incident light intensity $I_0$ if a predetermined condition is satisfied, so as to enable the measurement of the intensity of transmitted light on the basis of the light amount of the light source $3b$.

The light amount of the light source $3b$ may change due to deterioration or a usage environment. For example, if the light amount of the light source $3b$ decreases due to deterioration, then the light receiving element $3c$ will erroneously determine that the detection amount has decreased due to the influence of the coloring of the sensing film $2a$. For this reason, the incident light intensity $I_0$ providing the reference value of the measurement is required to be corrected, that is, $I_0$ is required to be reset. Steps S01 to S05 and S07 to S10 are the same as those of the control flow in FIG. 4, so that the description thereof will be omitted.

In step S05, the control unit determines a detection lower limit. If the hydrogen concentrations obtained by both measurement methods are below the detection lower limit, then the control unit proceeds to step S06A. Meanwhile, if hydrogen is of a concentration equal to or more than the detection lower limit, then the control unit proceeds to step S07.

If the hydrogen concentrations obtained by the two measurement methods are below the detection lower limit (YES in step S05), then the control unit sets the "status 0" (step S06A). Thereafter, the control unit proceeds to step S06B.

In step S06B, the control unit turns on an $I_0$ acquisition timer. The $I_0$ acquisition tuner is a timer used to determine whether the time at which the incident light intensity $I_0$ is to be acquired again (re-set) has been reached. The incident light intensity $I_0$ is not to be measured each time, and there are cases where numerical values stored in the hydrogen concentration measuring device 1 are obsolete. Hence, the incident light intensity $I_0$ is preferably updated, for example, every few days. Thereafter, the control unit proceeds to step S06C.

Then, the control unit determines whether $I_0$ setting time has been reached (step S06C). If the $I_0$ setting has been reached, the control unit proceeds to step S06D. Meanwhile, if the $I_0$ setting time has not been reached, then the control unit returns to step S03.

If the setting time has been reached (YES in step S06C), the control unit sets the current incident light intensity as $I_0$ (step S06D). This enables the hydrogen concentration measuring device 1 to measure an accurate hydrogen concentration without depending on the current light amount of the light source $3b$.

In short, the incident light intensity $I_0$ need to be updated when the light amount of the light source $3b$ increases or decreases. Therefore, an additional light receiving element (the light amount recognizing unit in the present invention) may be provided to recognize the light amount. In this case, when an increase or a decrease in the light amount is recognized, the current incident light intensity is re-set as $I_0$.

Referring now to FIG. 6, the fabrication method of the sensor chip 2 and the method for mounting the sensor chip 2 on the substrate 7 will be described.

(1) Preparing Sol-Gel Solution

A person fabricating the sensor chip 2 puts 100 ml to 150 ml of an ethanol solvent in a beaker made of alkali-free glass and stirs in a nitrogen atmosphere. Then, the fabricating person adds appropriate amounts of tungsten hexachloride $WCl_6$ and hexachloroplatinate (IV) hexahydrate $H_2PtCl_6 \cdot 6H_2O$ into the beaker to prepare a sol-gel solution.

(2) Applying the Sol-Gel Solution

The fabricating person sets a square transparent glass substrate (the light-transmissive substrate $2b$), one side thereof being approximately 1 cm, on a spin coater 20, and drops the sol-gel solution prepared in step (1) onto the glass substrate by a dropper 21 (refer to FIG. 6(a)). Then, the fabricating person rotates the spin coater 20 at 1500 rpm to 3000 rpm to evenly apply the sol-gel solution (refer to FIG. 6(b)). For the substrate, a visible-light-transmissive insulating substrate made of quartz, sapphire, zirconium oxide $ZrO_2$ or the like can be used.

(3) Drying the Thin Film

The fabricating person places the light-transmissive substrate $2b$, on which the sol-gel solution has been applied, in an electric oven 22 heated to 100° C., and heats the substrate $2b$ for approximately 30 minutes in air atmosphere. This dries the sol-gel solution, forming a coating layer (refer to FIG. 6(c)).

(4) Laminating the Coating Layer

The fabricating person repeats step (2) and step (3) thirty times to form a laminated coating layer having a thickness of approximately 300 nm. If used only for the electric resistance measurement (EM), then the sensing film may be as thin as a few hundred nm. If used also for the transmitted light intensity measurement (PM), then the detection accuracy can be improved by forming the laminated coating layer to a thickness of a few µm. The film thickness of the coating layer preferably ranges from 300 nm to 3 µm.

(5) Heat Treatment of the Coating Layer

The fabricating person places the coating layer deposited on the light-transmissive substrate 2b in the electric oven 22 heated to 400° C. to 500° C. and heats the coating layer for 10 minutes or more in air atmosphere. Thus, the sensing film 2a (Pt/WO$_3$ film) is formed. As the thin film for the sensing film, a vanadium pentoxide V$_2$O$_5$ film may alternatively be used.

(6) Forming the Comb-Shaped Electrodes and the Electrode Pads

The fabricating person forms, by sputtering, the pair of the comb-shaped electrodes 2a-1 and 2a-2 on the sensing film 2a, which has been formed in step (5), by using a patterning mask (refer to FIG. 6(d)). Although the electrodes preferably use indium tin oxide (ITO) as the material, platinum or palladium may be used, or platinum, palladium or gold may be coated over the electrodes.

Thereafter, by using a patterning mask for the electrode pads, the fabricating person forms the Ti/Au electrode pads (the square portions at the ends of the comb-shaped electrodes) by an electron beam deposition apparatus. A material, such as Ti/Pt/Au, Ni/Au or Ni/Pt/Au, may be used for the electrode pads.

(7) Forming the Reflection Film

The fabricating person forms, using the electron beam deposition apparatus, the Ti/Au reflection film 2c on the rear surface of the light-transmissive substrate 2b, on which the electrodes have been formed, thereby complete the sensor chip 2 (refer to FIG. 6(e)). A material, such as silver, copper, aluminum or rhodium, may be used for the reflection film 2c, with an adhesive layer made of nickel or titanium.

(8) Other (Cleaving the Work)

The fabricating person may fabricate a plurality of the sensor chips 2 on a large transparent glass substrate and cleave them by scribing and breaking after finishing step (7). The tungsten oxide porous body with diffused platinum, which is prepared as described above, has a small platinum particle size of a few nm to tens of nm, and also a small tungsten oxide grain boundary. In other words, the sensor chip 2 has a large area of contact with a gas to be measured, so that the speed of response to hydrogen is high. Further, the sensor chip 2 provides improved resistance to deactivation of platinum attributable to carbon monoxide.

The following will describe the method for mounting the sensor chip 2 on the substrate 7.

(9) Joining the Heater

A mounting person who mounts the sensor chip 2 on the substrate 7 prepares the heater 5, which is commercially available and which has, for example, a Nichrome wire or a carbon wire constituting a heating element laid on the inner side of an insulating ceramic plate, and which incorporates a temperature measuring element, such as a temperature measurement resistive element or a thermocouple. Formed on the surface of the heater 5 on which the sensor chip 2 is to be mounted is the joining pad 4b made of gold (Au).

The mounting person applies Au—Sn eutectic solder to the joining pad 4b (to form the joining member 4a), places the sensor chip 2 (the reflection film 2c side) thereon, and joins them by heating at 310° C. in a reflow furnace (refer to FIG. 6(f)). For the joining member 4a, a Sn-based solder may be used.

(10) Attaching the Sensor Chip to the Substrate

The mounting person installs the sensor chip 2 with the heater 5 attached thereto, by screwing, to the substrate 7, which is provided with the electrical measurement lines 7a to 7f, through the spacers 6 having a thickness of about a few hundred µm to about 1 mm (refer to FIG. 1).

(11) Wire Bonding

The mounting person electrically connects the electrode pads of the sensor chip 2, the heating power terminals 5a and the temperature measuring element terminals 5b of the heater 5, and the corresponding lines (the electrical measurement lines 7a to 70 of the substrate 7 by bonding with gold wires (refer to FIG. 1).

(12) Attaching the Optical Measurement Unit to the Substrate

The mounting person attaches the optical measurement unit 3 composed mainly of the optical measurement member package 3a and the optical measurement stay 3d to the substrate 7 by screwing. This completes the detector, which includes the sensor chip 2, of the hydrogen concentration measuring device 1 (refer to FIG. 1).

Referring now to FIG. 7A and FIG. 7B, a description will be given of the measurement of a hydrogen concentration in a non-oxidizing gas atmosphere.

The sensing film 2a (the Pt/WO$_3$ film) of the hydrogen concentration measuring device 1 exhibits electric resistance and coloring according to a hydrogen concentration also in a non-oxidizing gas atmosphere that does not contain oxygen. However, because of the absence of oxygen in the atmosphere, the electric resistance of the sensing film 2a is not reset and the coloring is retained even when the hydrogen concentration decreases.

The hydrogen concentration measuring device 1 has the configuration that makes it possible to alternately send a gas to be measured and atmospheric air corresponding to the reset gas in the present invention to the sensor chip 2 (the sensing film 2a), thus enabling the hydrogen concentration measuring device 1 to measure the hydrogen concentration. As illustrated in FIG. 7A, a port Pm and a valve Vm thereof and a port Pr and a valve Vr thereof are attached to the hydrogen concentration measuring device 1. Further, the control unit (the control arithmetic module 14a) supplies the gas to be measured through the port Pm to the sensor chip 2 and supplies the atmospheric air (or an inert gas that contains oxygen) through the port Pr.

FIG. 7B is a graph illustrating the relationship between time and the electrical conductivity (electric conductivity σ) of the sensing film 2a when a gas to be measured and the atmospheric air are alternately sent through the port Pm and the port Pr, respectively. The control unit first opens the valve Vm at time 0 and introduces the gas to be measured (e.g. N$_2$: 99.0%, H$_2$: 1.0%) through the port Pm. At this time, the electrical conductivity of the sensing film 2a immediately reaches 0.08 [S/cm], which is a value indicating approximately 90% of the peak, and then slowly increases.

Thereafter, the control unit closes the valve Vin and opens the valve Vr to introduce the atmospheric air (N$_2$: 80.0%, O$_2$: 20%) through the port Pr. This immediately resets the electrical conductivity of the sensing film 2a due to the influence of oxygen. When oxygen is sent toward the sensing film 2a, the electrical conductivity of the sensing film 2a returns temporarily to 0 [S/cm], as illustrated, so that there will be no value drift when a gas to be measured is introduced next time, thus enabling the hydrogen concentration measuring device 1 to accurately measure the hydrogen concentration.

The control unit thereafter performs measurement, alternately switching the gases sent out to the sensor chip 2 of the hydrogen concentration measuring device 1 by the valves Vin and Vr at each predetermined time. The configuration combined with the control for sending out gases makes it possible to measure the hydrogen concentration and reset the sensing film 2a, thus enabling the hydrogen concentration measuring device 1 to perform the measurement even when the hydrogen concentration changes in a non-oxidizing gas atmosphere. The relationship between time and absorbance A of the sensing film 2a indicates the same trend as that in FIG. 7B, and the transmitted light intensity returns temporarily to zero when the atmospheric air containing oxygen is introduced.

Second Embodiment

Lastly, a description will be given of the configuration of a hydrogen concentration measuring device 1' (composed mainly of a hydrogen sensor) according to a second embodiment with reference to FIG. 8A to FIG. 8C. The hydrogen concentration measuring device 1' is comprised mainly of a sensor chip 2' and an optical measurement unit 3', which are mounted on a substrate 7'. The same components (a sensing film, a light source and the like) as those in the first embodiment will be assigned the same reference numerals.

Figure 8A:
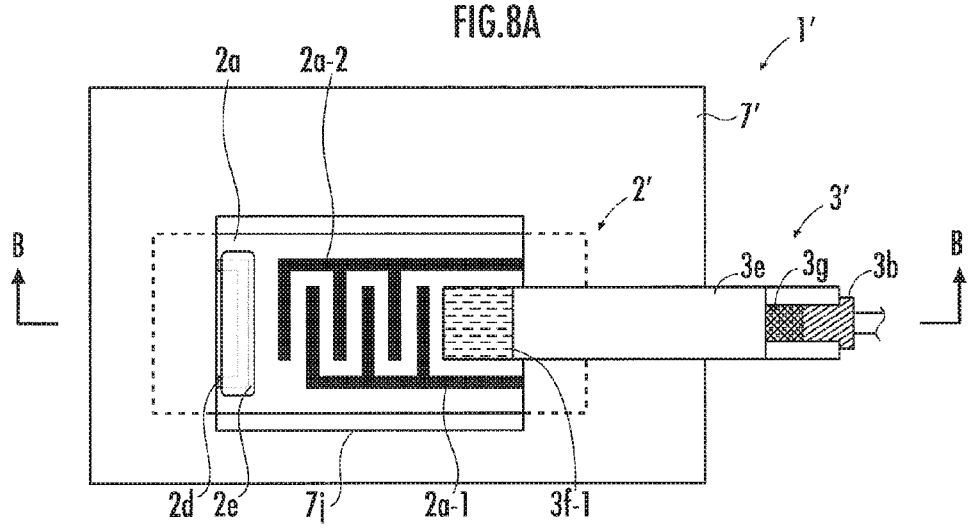
FIG. 8A is a configuration diagram (top view) of a hydrogen sensor according to a second embodiment of the hydrogen concentration measuring device.

FIG. 8A is a top view of a hydrogen sensor. In the sensor chip 2', a sensing film 2a (Pt/WO$_3$ film) is formed on the upper surface of a light-transmissive substrate 2b, and comb-shaped electrodes 2a-1 and 2a-2, a temperature measuring element 2d (e.g. a Pt—Rh temperature measurement resistive element) and a protective film 2e (e.g. a SiO$_2$ film), which are used for electric resistance measurement (EM), are provided on the surface of the sensing film 2a. The protective film 2e functions to prevent the electric resistance in the vicinity of the temperature measuring element 2d from decreasing.

Figure 8B:
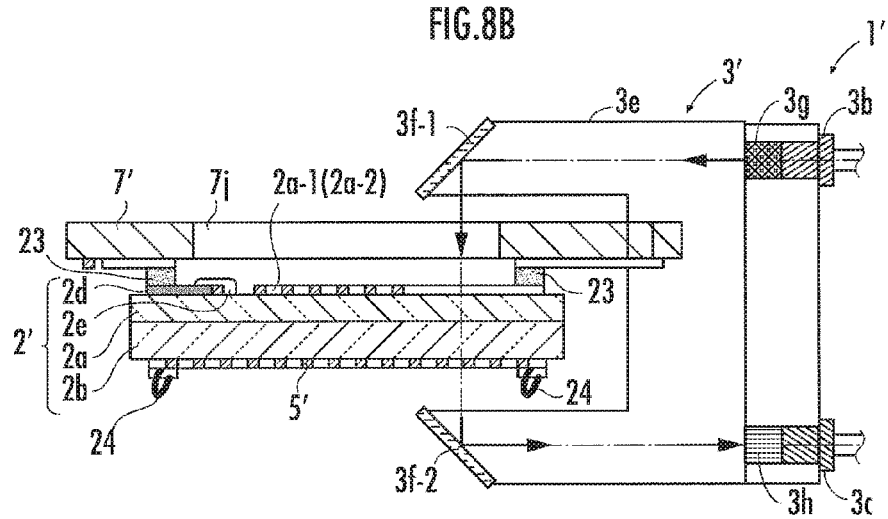
FIG. 8B is a configuration diagram (sectional view taken along line B-B in FIG. 8A) of the hydrogen sensor according to the second embodiment of the hydrogen concentration measuring device.
Figure 8C:
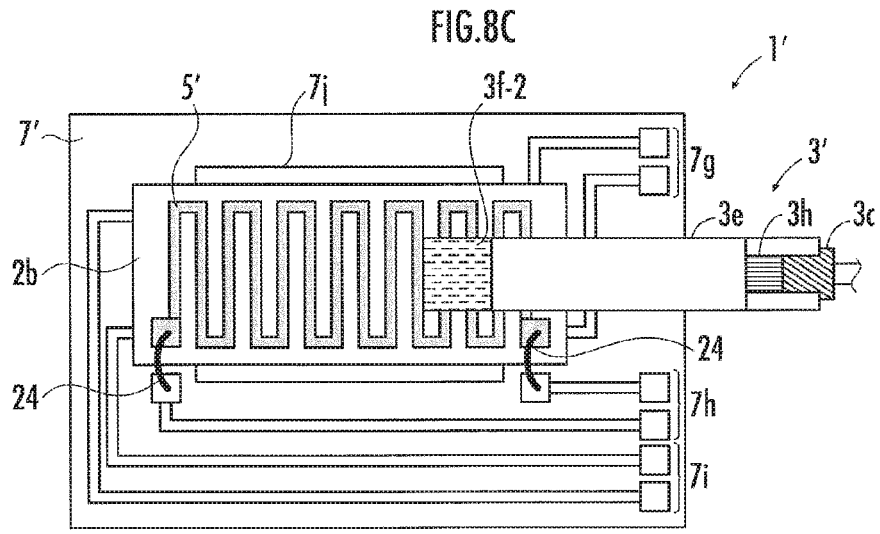
FIG. 8C is a configuration diagram (bottom view) of the hydrogen sensor according to the second embodiment of the hydrogen concentration measuring device.

Further, FIG. 8B is a sectional view taken along line B-B in FIG. 8A, and FIG. 8C is a bottom view of the hydrogen sensor. A heater wiring 5' is formed on the bottom surface of the light-transmissive substrate 2b. The heater wiring 5' is formed by sputtering an ITO film by using a patterning mask of a heater shape.

The substrate 7' is made of a material that has a thermal expansion coefficient close to that of the sensor chip 2'. Further, the substrate 7' is provided with an opening 7j of a size that allows the major part of the sensor chip 2' to be visually recognized. The bottom surface of the substrate 7' is provided with electrical measurement terminals 7g, heating power terminals 7h, temperature measuring element terminals 7i, and various types of wirings connected with these terminals. Further, the sensor chip 2' is joined to the substrate 7' by bumps 23 (e.g. gold (Au) members).

The comb-shaped electrodes 2a-1, 2a-2 and the temperature measuring element 2d on a sensing film 2a are electrically connected with the corresponding wirings (the wiring of the electrical measurement terminals 7g and the wiring of the temperature measuring element terminals 7i) on the substrate 7' through the bumps 23. Further, the heater wiring 5' on the rear surface of the sensor chip 2' is electrically connected to a corresponding wiring (the heating power terminals 7h) of the substrate 7' by wires 24.

The configuration in which the sensor chip 2' is connected to the substrate 7' by the bumps makes it possible to reduce the area of the heater wiring 5' thereby to suppress unwanted heat dissipation. Further, the bumps 23 provide a space between the sensor chip 2' and the substrate 7', thus adding to the heat insulation effect.

The foregoing configuration enables the temperature of the sensing film 2a to promptly increase and also enables the heater power to be suppressed. Further, the configuration in which the heater is directly deposited on the light-transmissive substrate 2b enables the light-transmissive substrate 2b and the sensing film 2a to be efficiently heated, so that the temperature of the sensing film 2a can be promptly increased.

The optical measurement unit 3' illustrated in FIG. 8B is comprised of a light source 3b, a light receiving element 3c, a light guide element 3e through which the observation light from the light source 3b passes, and reflection mirrors 3f-1, 3f-2. The optical measurement unit 3' is configured such that the observation light output from the light source 3b is bent 90° by the reflection mirror 3f-1, passes through the sensing film 2a, is further bent 90° by the reflection mirror 3f-2, and enters the light receiving element 3c. A collimate lens 3g is disposed at a light emitting part of the light source 3b, and a condenser lens 3h is disposed at a light incident part of the light receiving element 3c.

As described above, the hydrogen concentration measuring device 1' has the configuration in which the optical measurement unit 3' is mounted on the substrate 7' with the sensor chip 2' mounted thereon so as to permit the measurement of the transmitted light intensity of the sensing film 2a. Further, the substrate 7' with the sensor chip 2' mounted thereon and the light guide element 3e have a concavo-convex fitting structure. This structure makes it possible to easily and accurately determine a beam position when performing the transmitted light intensity measurement (PM) of the sensor chip 2'.

A modified example of the second embodiment may have a configuration in which a first unit comprised of a sensor chip 2', a substrate 7' and a light guide element 3e and a second unit comprised of a light source 3b and a light receiving element 3c are separate, and an optical fiber is used.

The second unit is separated and placed in an environment having an atmospheric temperature of less than several tens of degrees, because the light output of the light source 3b decreases and the sensitivity (S/N ratio) of the light receiving element 3c decreases in a high temperature atmosphere of several tens of degrees. This arrangement permits highly accurate measurement of the transmitted light intensity of a sensing film 2a.

As described above, the hydrogen concentration measuring device 1 (1') includes the sensor chip 2 (2') that detects the electric resistance of the sensing film 2a, and the optical measurement unit 3 (3') that detects the transmitted light intensity of the sensing film 2a. The first measurement range (the low concentration range), in which the electric resistance can be detected by the electric resistance detector, and the second measurement range, in which the transmitted light intensity can be detected by the transmitted light intensity detector, partly overlap. The control unit performs the measurement value correction processing whereby to reduce the difference between a hydrogen concentration measured from an electric resistance and a hydrogen concentration measured from a transmitted light intensity. Thus, hydrogen concentrations over an extensive range can be measured with high accuracy.

The foregoing embodiments are examples of the embodiments of the present invention and a variety of modified examples are conceivable in addition to the foregoing embodiments. For example, the sensing film may use a vanadium pentoxide, and the comb-shaped electrodes and the reflection films may use various other materials.

Basically, the electric resistance measurement (EM) and the transmitted light intensity measurement (PM) are both performed to measure a hydrogen concentration. Alternatively, however, the measurement method may be switched according to a hydrogen concentration. In the control flow of FIG. 5A, the transmitted light intensity measurement (PM) is turned off in the first measurement range, in which the electric resistance measurement (EM) is possible. Conversely, the electric resistance measurement (EM) may be turned off in the second measurement range, in which the transmitted light intensity measurement (PM) is possible. In the control flow of FIG. 5B, the $I_0$ setting time is a predetermined time established beforehand. Alternatively, however, the setting time may be appropriately determined according to an environment or the like.

The measurement range of the electric resistance measurement (EM) and the measurement range of the transmitted light intensity measurement (PM) are required to overlap even if only by a small part thereof. In the overlapped range, a hydrogen concentration is calculated from a weighted average value (or an average value) of the values obtained by the two measurement methods, thus minimizing the possibility of the occurrence of a difference in concentration when switching the measurement method.

DESCRIPTION OF REFERENCE NUMERALS 1, 1' . . . Hydrogen concentration measuring device, 2, 2' . . . Sensor chip (Electric resistance detector), 2a . . . Sensing film, 2a-1, . . . Comb-shaped electrode, 2b . . . Light-transmissive substrate, 2c . . . Reflection film, 3, 3' . . . Optical measurement unit (Transmitted light intensity detector), 3a . . . Optical measurement member package, 3b . . . Light source, 3c . . . Light receiving element, 3d . . . Optical measurement stay, 4 . . . Joining part, 4a . . . Joining member, 4b Joining pad, 5 . . . Heater, 5' . . . Heater wiring, 6 . . . Spacer, 7, 7' . . . Substrate, 7a to 7f . . . Electrical measurement wiring, 8 . . . Electrical measurement connector, 9 . . . Optical measurement connector, 10 . . . Measurement unit, 11 . . . Transmitted light intensity measurement unit, 12 . . . Electric resistance measurement unit, 13 . . . Heater control unit, 14 . . . Measurement management unit, and 15 . . . External input/output unit.

What is claimed is:

1. A hydrogen concentration measuring device comprising:
a sensing film which is configured by including a metal oxide film and which is placed in a gas atmosphere;
an electric resistance detector which detects an electric resistance of the sensing film;
a transmitted light intensity detector which detects a transmitted light intensity of the sensing film; and
a controller which performs:
first hydrogen concentration measurement processing whereby to measure a hydrogen concentration in the gas atmosphere based on an electric resistance detected by the electric resistance detector in a first measurement range,
second hydrogen concentration measurement processing whereby to measure the hydrogen concentration in the gas atmosphere based on the transmitted light intensity detected by the transmitted light intensity detector in a second measurement range having at least a part thereof overlapping with the first measurement range, and
measurement value correction processing in which processing for reducing a difference between a hydrogen concentration measured by the first hydrogen concentration measurement processing and a hydrogen concentration measured by the second hydrogen concentration measurement processing is carried out thereby to determine a measurement value of a hydrogen concentration in a range in which the first measurement range and the second measurement range overlap.

2. The hydrogen concentration measuring device according to claim 1,
wherein the controller calculates a weighted average value of a measurement value obtained by the first hydrogen concentration measurement processing and a measurement value obtained by the second hydrogen concentration measurement processing as the processing for reducing the difference and determines the weighted average value as the measurement value of the hydrogen concentration in the measurement value correction processing.

3. The hydrogen concentration measuring device according to claim 1,
wherein the controller stops the operation of the transmitted light intensity detector and measures a hydrogen concentration by the first hydrogen concentration measurement processing in the case where the hydrogen concentration is included in the first measurement range.

4. The hydrogen concentration measuring device according to claim 1, comprising:
a light amount recognizing unit which recognizes a light amount of a light source,
wherein the transmitted light intensity detector re-sets a reference value of the light amount in the case where an increase or a decrease in the light amount is recognized by the light amount recognizing unit.

5. The hydrogen concentration measuring device according to claim 1, comprising:
a reset gas feeder which sends out a reset gas for resetting a hydrogen concentration to the sensing film,
wherein the controller actuates the reset gas feeder in the case where a hydrogen gas concentration is measured in a non-oxidizing gas atmosphere.

* * * * *